(12) United States Patent
Iwamoto et al.

(10) Patent No.: US 6,699,388 B1
(45) Date of Patent: Mar. 2, 2004

(54) FILTER DEVICE AND METHOD FOR PROCESSING BLOOD

(75) Inventors: Ushio Iwamoto, Oita (JP); Junsuke Suemitsu, Oita (JP); Makoto Yoshida, Oita (JP)

(73) Assignee: Asahi Medical Co., Ltd., Tokyo (JP)

( * ) Notice: Subject to any disclaimer, the term of this patent is extended or adjusted under 35 U.S.C. 154(b) by 0 days.

(21) Appl. No.: 09/700,031

(22) PCT Filed: May 13, 1999

(86) PCT No.: PCT/JP99/02478

§ 371 (c)(1),
(2), (4) Date: Nov. 9, 2000

(87) PCT Pub. No.: WO99/58172

PCT Pub. Date: Nov. 18, 1999

(30) Foreign Application Priority Data

May 13, 1998 (JP) .......................................... 10-146717
Apr. 2, 1999 (JP) .......................................... 11-130416

(51) Int. Cl.⁷ .......................... B01D 29/48; B01D 63/10
(52) U.S. Cl. ........................... 210/497.1; 210/321.74; 210/321.83; 210/488; 210/489; 210/496
(58) Field of Search ................... 210/321.74, 321.83, 210/488, 437, 489, 493.4, 493.5, 496, 497.01, 497.1, 498, 499, 650, 651, 767

(56) References Cited

U.S. PATENT DOCUMENTS

| | | | | | |
|---|---|---|---|---|---|
| 3,668,837 A | * | 6/1972 | Gross | ........................... | 210/96 |
| 4,022,692 A | * | 5/1977 | Janneck | ....................... | 210/494 |
| 4,028,250 A | * | 6/1977 | Loft | ............................ | 210/259 |
| 4,253,962 A | * | 3/1981 | Thompson | ................... | 210/414 |
| 4,551,435 A | * | 11/1985 | Liberti et al. | ................ | 436/541 |
| 4,606,824 A | * | 8/1986 | Chu et al. | .................... | 210/635 |
| 4,701,267 A | * | 10/1987 | Watanabe et al. | ........... | 210/806 |
| 4,834,881 A | * | 5/1989 | Sawada et al. | ........ | 210/321.74 |
| 4,872,990 A | * | 10/1989 | Van Wijk | .................... | 210/644 |
| 5,266,195 A | * | 11/1993 | Hopkins | ................ | 210/321.74 |
| 5,748,437 A | * | 5/1998 | Andelmann | .............. | 210/198.2 |

FOREIGN PATENT DOCUMENTS

| | | | |
|---|---|---|---|
| EP | 352917 | * | 1/1990 |
| JP | 2-46858 | | 2/1990 |
| JP | 2-71837 | | 3/1990 |

* cited by examiner

*Primary Examiner*—John Kim
(74) *Attorney, Agent, or Firm*—Young & Thompson

(57) ABSTRACT

A filter for filtering blood includes a coiled core with a hollow center. The core has only two layers that are coiled atop one another, the two layers being a blood filter layer and a spacer layer where blood flows more easily through the spacer layer than through the filter layer. An outer side of one of the spacer layer, and the filter layer defines an outer circumference of the core. The filter and spacer layers are coiled so that both sides of the filter layer directly contact respective sides of the spacer layer. A casing for the core has a blood inlet in fluid communication with the outer circumference of the core and a blood outlet in fluid communication with the hollow center. Blood entering the inlet travels to the outlet within the spacer layer and transversely across the filter and spacer layers.

27 Claims, 6 Drawing Sheets

FILTER DEVICE AND METHOD FOR PROCESSING BLOOD

TECHNICAL FIELD

The present invention relates to a blood treating filter equipment incorporating a filter material to remove specific components efficiently from a large amount of blood.

BACKGROUND ART

Recently, a requirement has been imposed for a technology to remove a specific protein, leucocyte and the like contained in blood for the purposes of a blood extracorporeal blood perfusion therapy for autoimmune diseases or inflammatory bowel diseases such as systemic lupus erythematosus, chronic or malignant articular rheumatism, multiple sclerosis, ulcerative colitis and Crohn's disease, or diseases such as leukemia and cancer, or immunosuppression before an organ transplantation operation.

The blood treating filter equipment used for these applications is required to have not only a high removability but at the same time an ability to treat a large amount (about 2 to 5 liters) of blood.

Until now, for example, a flat plate type nonwoven fabric filter composed of extra fine fiber or an equipment in which the filter is wound cylindrically (JP-A-62-243561) have been proposed as a leucocyte removal filter equipment. However, in a treatment of a large amount of blood as described above with these filters, a flow rate has to be reduced due to a possible large pressure loss in the equipment depending on a condition of the blood to be treated or when an anticoagulant is added insufficiently or mixed inadequately. This leads to a prolonged treatment time. Thus, a further improvement in removal efficiency has been required.

The inventors earnestly studied for a cause of the above-mentioned rise of the pressure loss in a filter. As a result, the following were revealed. In a conventional filter, large amounts of an object to be removed are trapped in the narrow channels in the filter impairing a smooth blood flow and increasing pressure. However, the rise of the pressure loss in a filter was not brought about as a result of an object to be removed as found in a conventional filter, but instead by characteristics specific to blood. In other words, the inventors found that the rise of the pressure loss was caused by platelets and other coagulation factors in blood which were activated by their sudden contact with a filter material forming a blocking membrane, disturbing a smooth blood low.

To avoid the,.problem described above, it is considered to be effective to enlarge a surface area of the filter. However, a simple enlargement of a filter size extremely impairs operability and productivity of the equipment. Furthermore, an enlargement of a surface area of a filter within a fixed volume of a filter material according to a conventional method lowers a removal efficiency for an object, due to a reduced filter thickness.

DISCLOSURE OF THE INVENTION

In view of the points described above, an object of the present invention is to provide a blood treating filter equipment with a high ability to avoid a pressure rise, which can inhibit local and abrupt activations of coagulation factors in blood, and remove target substances to be removed from a large amount of blood with a high efficiency without reducing a treating rate.

In order to achieve the object described above, the present invention comprises the following (1) and (2).

(1) A filter material, in which the following (a) and (b) are wound in an overlapped state, an end part of (b) is exposed to an outer circumferential surface or an inner circumferential surface of the filter material, and both end faces of the filter material are sealed liquid-tightly, wherein, (a) is a blood treating filter layer, and (b) is a sheet-like spacer layer through which blood flows more easily compared with said blood treating filter layer.

(2) A casing in which the filter material described above is installed, wherein the casing has a blood inlet and a blood outlet, the blood inlet leads to the side of an exposed end part of (b) on an outer circumferential surface or an inner circumferential surface of the filter material described above, and the blood outlet leads to the opposite side to the blood inlet on an inner circumferential surface or an outer circumferential surface of the filter material described above.

BEST MODE FOR CARRYING OUT THE INVENTION

Figure 1A:
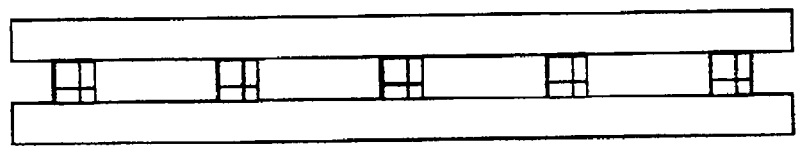
FIG. 1A is an example showing a state in which a spacer layer is substantially continuous.

The term "blood treating filter layer" in the present invention means a filter layer which can remove a specified blood cell, protein or the like from a body fluid such as blood, and preferably a filter layer which can selectively capture a blood cell, protein or the like as an object to be removed.

As a form of the filter layer, those considered are such as a nonwoven fabric, a woven cloth, a sheet of porous body or a sheet-like bag packed with particles. In the case when an object to be removed is leucocyte, a nonwoven fabric or a porous body gives preferable results from the view point of removal efficiency.

The term "nonwoven fabrics" means a fabric structure made of an assemblage of fibers composed of one or more layers without weaving and knitting. As a material for a fiber, a synthetic fiber, an inorganic fiber or the like is used. Among them, a synthetic fiber, for example, fibers of polyethyleneterephthalate, polybutyleneterephthalate, nylon, polypropylene, polyethylene, polystyrene, polyacrylonitrile and the like are preferably used.

A mean diameter of a fiber constituting the nonwoven fabric is not less than 0.3 $\mu$m and less than 5.0 $\mu$m, preferably not less than 0.4 $\mu$m and not more than 4.5 $\mu$m, more preferably not less than 0.5 µm and not more than 4.0 µm. A mean diameter less than 0.3 µm reduces a fluidity of blood resulting in a large pressure loss in an equipment, and that not less than 5.0 µm impairs a blood treating performance such as a leucocyte removal rate.

The mean diameter of a fiber constituting the nonwoven fabric of the present invention can be obtained, for example, by taking a photograph of fibers constituting a nonwoven fabric using a scanning electron microscope, measuring diameters of 100 or more fibers chosen at random and calculating an arithmetical mean value of them.

And the term "porous body" in the present invention means a structure having a continuous constitution like a three dimensional network with continuous open cells. Material for the porous body is not specially limited and includes a natural high polymer such as cellulose and its derivatives or a polymer material such as polyolefin, polyamide, polyimide, polyurethane, polyester, polysulfone, polyacrylonitrile, polyethersulfone, poly(meth)acrylate, butadiene-acrylonitrile copolymer, ethylene-vinylalcohol copolymer and polyvinylacetal, or mixture thereof.

A mean pore size of the porous body is not less than 1.0 µm and not more than 60 µm, preferably not less than 2.0 µm and not more than 55 µm, more preferably not less than 3.0 µm and not more than 50 µm. A mean diameter smaller than 1.0 µm reduces a fluidity of blood resulting in a rise of a pressure loss in an equipment, and that larger than 60 µm impairs a blood treatment performance such as a leucocyte removal rate.

The mean pore size in the present invention is a value obtained by measuring by a pressure mercury penetration method. The mean pore size is obtained from a peak (mode) of a graph showing differential volume of fine pores on an axis of ordinate and pore size on an axis of abscissa by the pressure mercury penetration method, for example, measuring with Poresizer 9320 made by Shimazu Corp. For measurement data by the pressure mercury penetration method, the data measured at the pressure range of 1–2650 psia are used.

In addition, in order to reduce a capture rate for platelet and enable a selective adsorption and capture for a target substance, a substrate surface of a blood treating filter layer may be coated or grafted with a polymer less capable of capturing platelets. A ligand capable to selectively adsorb a specified component such as blood cell or plasma protein may also be coated or immobilized.

The term "thickness" of the blood treating filter layer used in the present invention is defined as the shortest distance when a line connecting a given contacting face between a blood treating filter layer and a spacer layer and another contacting face of an adjacent layer crosses over the blood treating filter layer only. This thickness is not less than 0.1 mm and not more than 10.0 mm, preferably not less than 0.15 mm and not more than 8.0 mm, more preferably not less than 0.2 mm and not more than 5.0 mm, though it depends on the diameter of filter or the mean pore size. A thickness of a filter layer more than 10.0 mm reduces a length of the filter layer when the filter layer is wound cylindrically within a limited volume of a filter material, also reduces the length of the spacer layer to be overlapped, and thus makes it difficult to avoid a pressure rise. Also, a thickness less than 0.1 mm extremely restricts a volume of the filter layer of the portion to be overlapped with the spacer layer resulting in a poor blood treating performance such as a leucocyte removability.

The blood treating filter layer may be composed of only one sheet-like filter layer or several sheet-like filter layers of the same kind or multiple kinds.

The term "spacer" layers in the present invention is a layer through which blood flows more easily compared with the blood treating filter layer, and those used are such as a coarse net-like metal, a synthetic resin, an inorganic fiber, a synthetic fiber, or a nonwoven fabric made of a fiber having a diameter larger than a nonwoven fabric used in the blood treating filter layer and the like. The spacer layer is overlapped and wound together with the blood treating filter layer to create a space where blood flows easier between the blood treating filter layers. Preferably a width of the spacer layer is almost the same as that of the blood treating filter layer, provided that length means the whole length of the spacer layer along a winding direction and width means a length in a perpendicular direction to the winding direction.

Figure 1B:
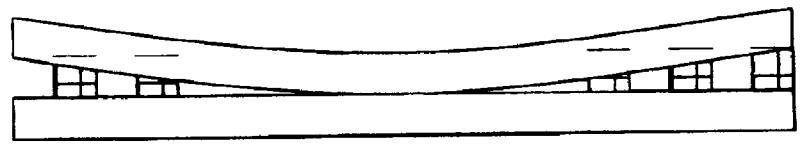
FIG. 1B is an example showing a state in which a spacer layer is discontinuous.

The spacer layer may be composed of only one sheet or several sheet-like materials of the same kind or multiple kinds similar to the blood treating filter layer described above, but it is important that the spacer layer is substantially continuous in the filter material. Here, the term "substantially" continuous means that any portion of the spacer layer is connected continuously without an interruption by the blood treating filter layer. Even if the spacer layer itself is not continuous as shown in FIG. 1A, a gap structure formed by winding a filter material can be substantially continuous unless the gap structure is intercepted by the blood treating filter layer. The spacer layer can become discontinuous as shown in FIG. 1B, but in the present invention, only a substantially continuous part from a blood inlet side is called a spacer layer, and a part in a downstream from the portion intercepted by a blood treating filter layer is not called a spacer layer.

The term "volume ratio of spacer section" in the present invention means a ratio of a volume occupied by a spacer section to a volume occupied by a filter section. If a thickness of the spacer section is uniform and a filter material is cylindrical, then the volume ratio of spacer section is expressed by the formula (1) described hereinbelow. The term "spacer section" means a portion of the spacer layer sandwiched by the blood treating filter layers in its inner and outer sides and leading to the blood inlet side, except a part exposed on the outermost or innermost circumferential surfaces of the filter material or a part disconnected from the blood inlet side in the filter material. The volume of the spacer section is calculated as a volume of the spacer section supposing that it is sheet-like. The term "filter sections" in the present invention means a part of the filter corresponding to a part of the spacer material except the part of the spacer layer exposed on the outermost or innermost circumferential surfaces.

$$\text{Volume ratio of spacer section} = \text{Volume of spacer section } [L \times n \times d] / \text{Volume of filter section } [V] \quad (1)$$

wherein, $$\text{Volume of filter section } [V] = L \times \pi \times (R^2 - r^2)$$

R and r are calculated based on the lengths of the circumferences of the outermost and innermost layers of a blood treating filter layer, respectively, supposing that a cross-section of the filter material is round having a radius.

R: Radius of: the outermost circumferential layer of the filter section (mm)

r: Radius of the innermost circumferential layer of the filter section (mm)

L: Width of the filter section (=Width of the spacer section) (mm)

V: Volume of the filter section (mm$^3$)
d: Thickness, of the spacer section (mm)
n: Length of the spacer section (mm)

The value of the volume ratio of spacer section is not less than 0.3 and not more than 0.7, preferably not less than 0.35 and not more than 0.65, and more preferably not less than 0.4 and not more than 0.6. The value of the volume ratio of spacer section less than 0.3 reduces an ability to avoid a pressure rise. The value over 0.7 decreases a volume of a blood treating filter layer, and impairs a blood treatment performance such as leucocyte removability because it decreases a frequency of a contact of blood with a blood treating filter layer due to an overwhelmingly increased blood flow to a spacer layer.

The term "spacer thickness" as used in the present invention means the shortest distance when a line connecting a given contacting face between a blood treating filter layer and a spacer layer and another contacting face of an adjacent layer crosses over the spacer layer only, and is not less than 0.5 mm and not more than 2.0 mm, preferably not less than 0.6 mm and not more than 1.9 mm, and more preferably not less than 0.7 mm and not more than 1.8 mm. The value of the spacer thickness less than 0.5 mm reduces an ability to avoid a pressure rise. The value over 2.0 mm decreases a volume of a blood treating filter layer, and impairs a blood treating performance such as leucocyte removability because it decreases a frequency of a contact of blood with a blood treating filter layer due to an overwhelmingly increased blood flow to a spacer layer.

Figure 2:
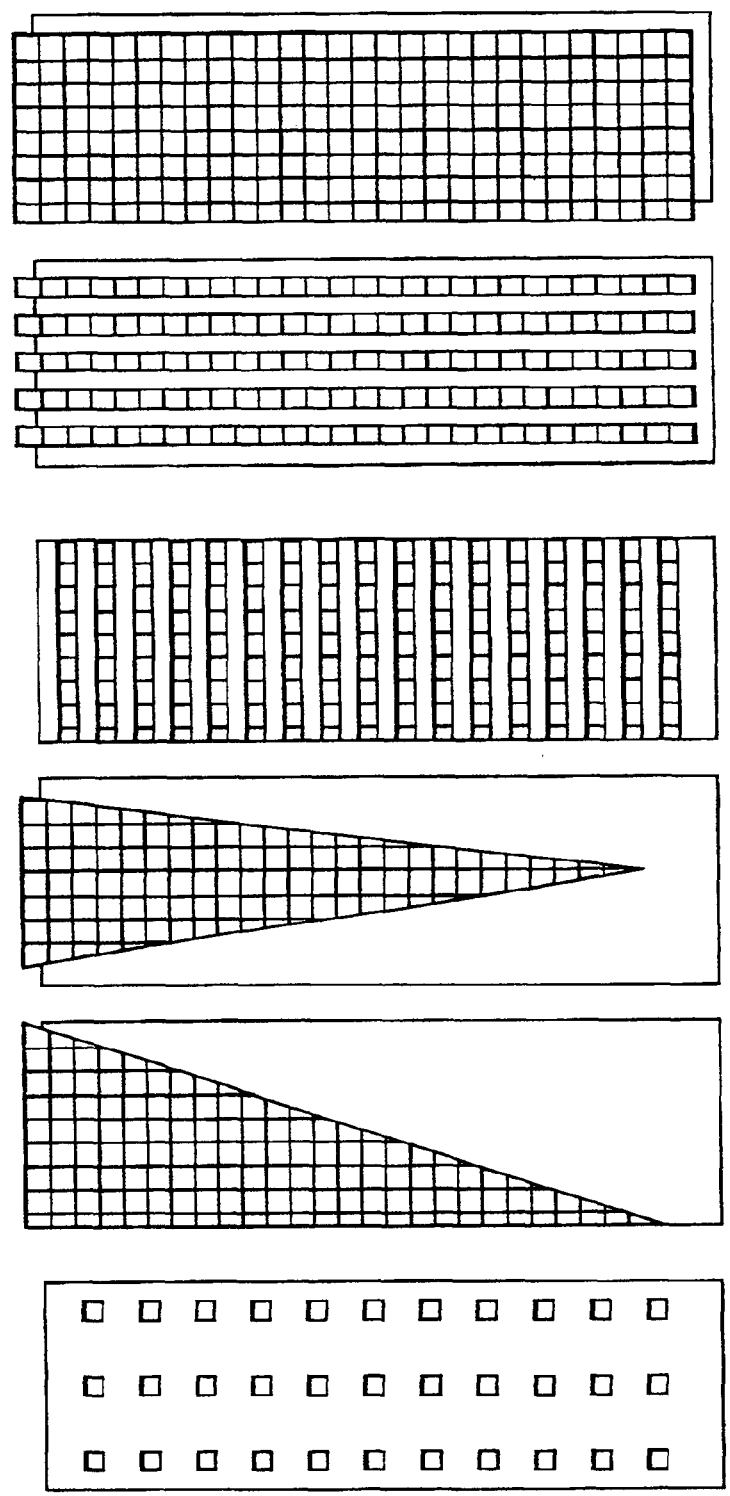
FIG. 2 shows an example of actual spacer layers.

Furthermore, the spacer section may have forms such as illustrated in FIG. 2, and is overlapped with a blood treating filter layer. In FIG. 2, blank rectangles in the background express blood treating filters, and assemblages of small squares drawn on them express spacer layers, respectively. Preferably, a width of the spacer section is almost the same as that of the blood treating filter layer provided that length means the whole length along a winding direction of the layer and width means a length along a perpendicular direction to the winding direction. A length of the spacer section is not necessarily almost the-same as that of the blood treating filter layer, but a length from an end at a blood inlet side where at least overlapping with a blood treating filter layer starts may be about ½ or more, preferably ⅔ or more, and more preferably ¾ or more of the whole length of a blood treating filter layer. If the length of an overlapped spacer layer to a blood treating filter layer is shorter than this, a desired avoidance for a pressure rise can not be attained in a blood treatment.

In order to recover blood from the equipment after a blood treatment is finished, blood is sometimes pushed out by air pressure by introducing air into the equipment instead of flowing an aqueous solution such as saline. In consideration of such an operation, a structure in which the entire circumferential surface on the blood outlet side of a filter section is covered with a filter layer is desirable for easier recovery of blood remaining in the equipment, because a blood treatment can be finished within a short period. On the other hand, a structure in which a spacer layer is exposed at both of an outer and an inner ends of the filter section is most desirable to achieve more superior ability for avoiding a pressure rise besides keeping a high blood treatment performance such as a leucocyte removability. That is, this structure has a high blood treatment performance such as a leucocyte removability although an outer and an inner circumferential layers of the filter section are communicating with each other through a spacer layer.

The spacer layer exhibits the effects mentioned above by exposing its end at a blood inlet side of a blood treating filter layer. When a blood inlet side is on the outer circumferential surface side, a material constituting a spacer layer may be extended from a space between blood treating filter layers and exposed on an outer circumferential surface of a filter material, and used as a support continuously covering a whole area of the outer circumferential surface of the filter material (Refer to (9) in FIG. 4. Since a uniform space corresponding to a thickness of the support is created between an inside wall of a case and a blood treating filter layer by the presence of the support on a whole area of an outer circumference surface like a spacer layer, introduced blood to be treated can easily spread to the whole area of the outer circumferential surface of the filter material. Preferably such a support is continuous to a spacer layer from the view point of easy manufacturing, but may be wound on the outer circumferential surface of the filter material independently from the spacer layer. As such a support, a mesh and the like having many apertures to make blood flow easier than through a blood treating filter layer can be used.

Figure 3:
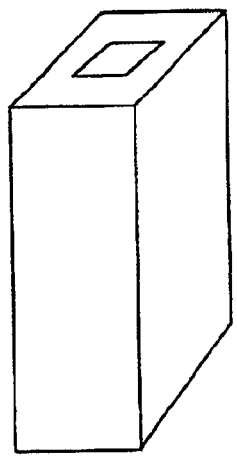
FIG. 3 shows an example of actual cylindrical shapes of a filter material.
Figure 3:
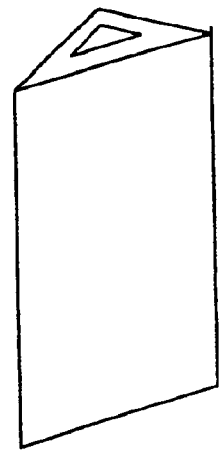
Figure 3:
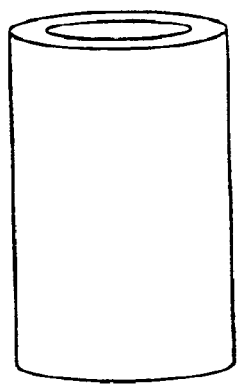
Figure 3:
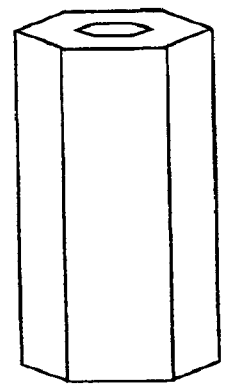
Figure 3:
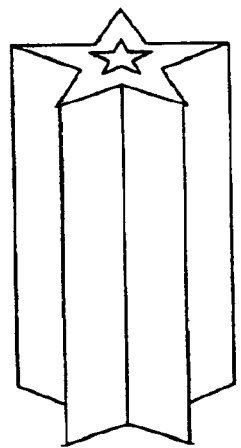
Figure 3:
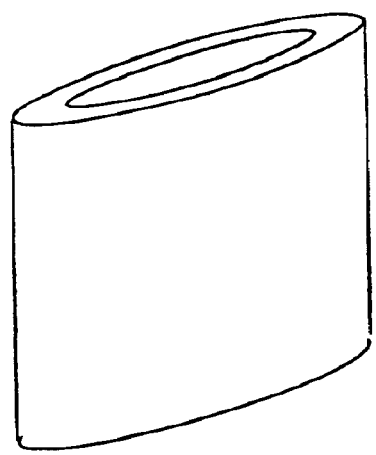

The present invention is new described mainly for a case in which a blood inlet side is on the outer circumferential surface side of a filter material as an example. A filter material composed of a blood treating filter layer and a spacer layer is, for example, wound in a hollow cylindrical shape having a cylindrical space in a central part. The hollow part inside of the filter material becomes a channel for blood recovery after components to be removed such as leucocytes are eliminated-from blood. Any shape of the hollow cylinder may be accepted as illustrated in FIG. 3, but a cylindrical shape is the most preferable from the view point of a fluidity of blood through the spacer layer and productivity of the filter material. Size of the filter material cannot be determined unconditionally because it depends on an amount of blood to be treated and a structure of the filter material to be adopted, but roughly an outer diameter of 30–50 mm and a height of 100–250 mm is preferable for treating approximately 3 liters of blood.

A ratio of an outer diameter to a length between both end faces of the cylindrical filter material is desirably around 1:10–1:2. Within a fixed volume of a filter material, the length between both end faces shorter than 1:2 reduces an ability to avoid a pressure rise-because a flow of blood to a spacer layer is restricted due to a narrowed entrance into a spacer layer. The length between both end faces longer than 1:10 lowers a performance because of a reduced thickness of a blood treating filter layer, and makes it difficult to wind a blood treating filter layer together with a spacer layer.

Figure 4:
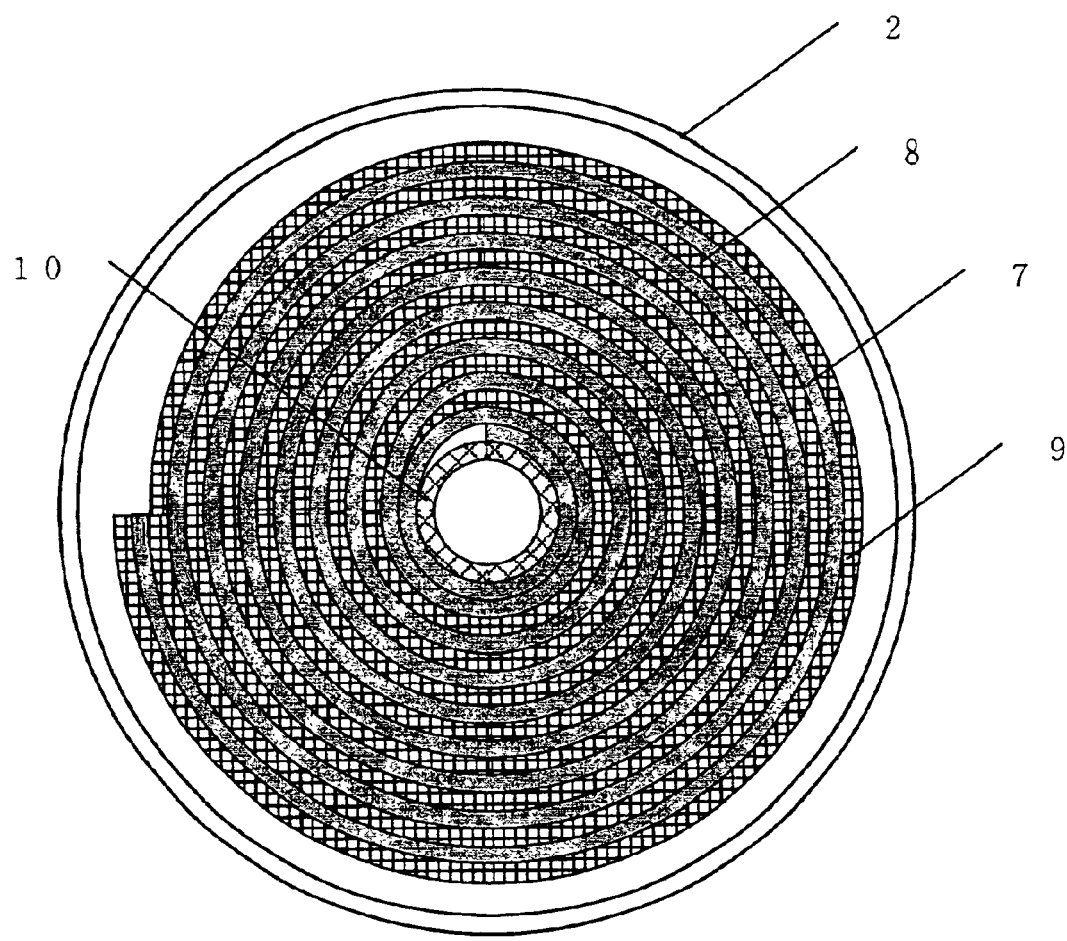
FIG. 4 is a schematic drawing of a transverse cross-section showing an example of the blood treating filter equipment of the present invention.
Figure 5:
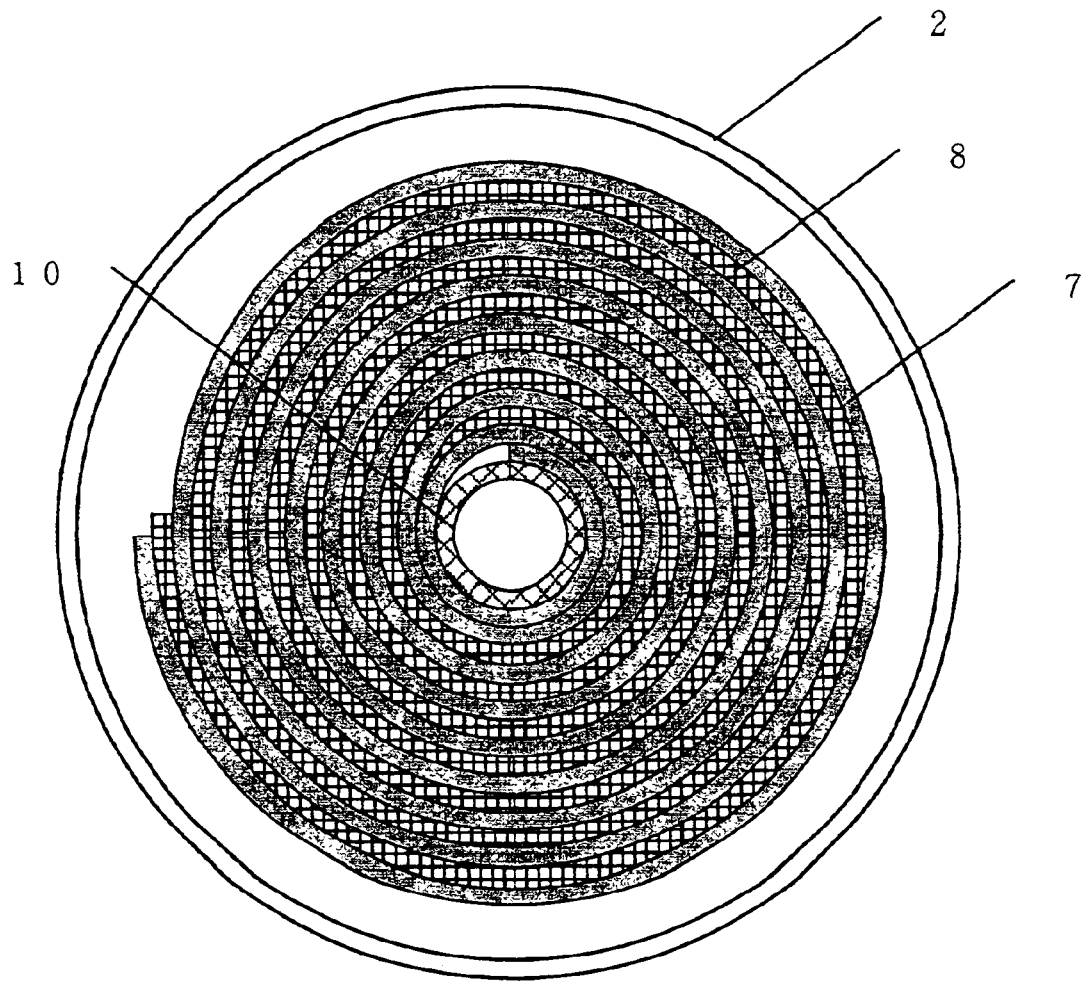
FIG. 5 is a schematic drawing of a transverse cross-section showing an example of the blood treating filter equipment of the present invention.

In a hollow space in the center of a filter material, preferably a support contacts an inner circumferential surface [(10) in FIGS. 4 and 5] and consists of a pipe and the like having a mesh or a porous part in order to support an inner circumferential surface of a filter material and creame a hollow space. The size of the hollow section of a filter material should be properly determined depending on a size of the filter material, that is, an outer diameter, a thickness and the like of the filter material.

In the present invention, the filter material is installed in a cylindrical case having a similar size, and both end faces are liquid-tightly sealed so that blood cannot pass through. For sealing, a material which has a superior compatibility in contact with blood and is suitable for liquid-tight sealing may be used. More specifically, a known synthetic resin such as a urethane and a silicone can be used.

A blood inlet may be located in any desired position of the case so long as blood to be treated can be fed therefrom to the outer circumferential surface side of the filter material having both ends sealed. Preferably it should be located in an uppermost part of a cylindrical case so that blood to be treated can evenly flow into the outer circumferential surface of the filter material and be dispersed radially for the filter material to be efficiently utilized.

Figure 6:
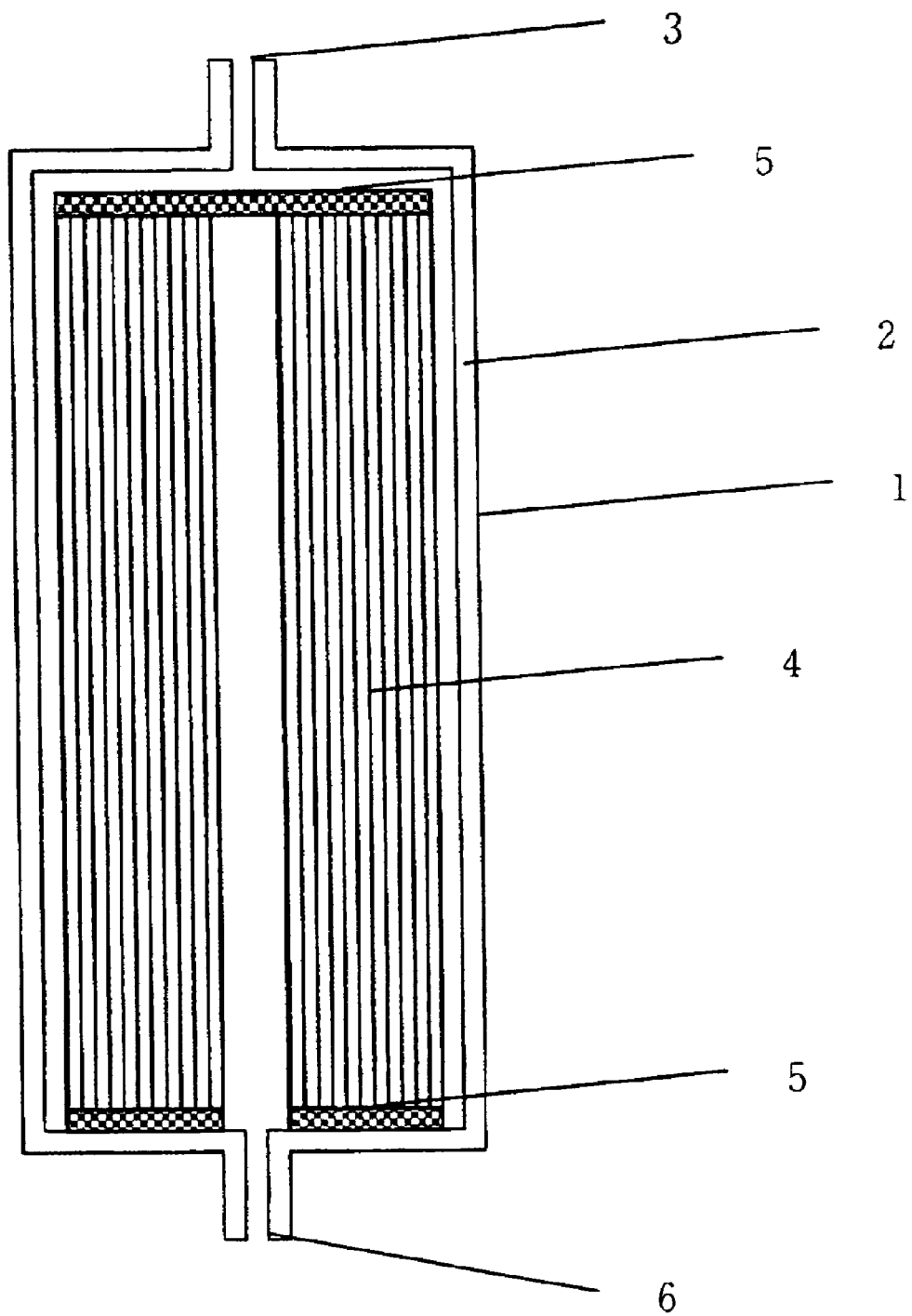
FIG. 6 is a schematic drawing of a longitudinal cross-section showing an example of the blood treating filter equipment of the present invention.

An embodiment of the blood treating filter equipment of the present invention is now explained more specifically using FIGS. 4–6.

The blood treating filter equipment 1 is composed of the filter material 4 wound in a hollow cylindrical shape and the case 2 having the blood inlet 3 and the blood outlet 6. The filter material is liquid-tightly sealed at both end faces with the adhesive 5, and installed in the case 2 so that its outer side and inner side communicate with the blood inlet 3 and the blood outlet 6, respectively.

The blood to be treated flows into the blood treating filter equipment 1 from the blood inlet 3. Both end faces of the hollow cylindrical filter material 4 are liquid-tightly sealed and the blood cannot pass through. Therefore, through the outermost layer of the blood treating filter layer 7, the outermost layer of the spacer layer 8 or an outer end of the spacer layer 8 which is constituting an outer circumferential surface of the filter material, the blood gradually permeates into the inside of the filter material with components to be removed being captured, gathers in a hollow part at the center of the filter material after passing through the cylindrical filter material, and exits from the equipment through the blood outlet 6 communicating with the hollow part.

The flow of blood in the filter material is a combined stream of two components: a flow that penetrates into the blood treating filter layer 7 accompanied with the capture or removal of components to be removed such as leucocyte, and another flow that runs along the spacer layer 8. As a result, the blood spreads to both the outer and inner circumferential parts of the filter material soon after starting a a treatment, and a sharply reduced flow resistance enables a continuation of a smooth and efficient removal of the objects throughout the whole period of time from the start to the end of the treatment.

By the actions described above, a blood flow spirally penetrating toward an inner circumferential surface of the cylindrical filter along with the spacer layer in addition to a blood flow crossing over the blood treating filter layers in an outer part of the filter material can enlarge a contact area between blood and the blood treating filter layer in the initial stage of the start of the treatment. It is believed that this enables inhibiting a local and abrupt activation of blood coagulation components caused by a gathering: of the blood into a narrow surface area of the filter. Furthermore, even when a blood treating filter layer located in an outer circumferential surface side of the filter material is blocked, since another blood flow channel to an inner circumferential surface side of the filter material has been created, a pressure loss does not rise and a treating rate can be kept constant until the end of a treating period.

The present invention will now be explained more concretely by Examples.

EXAMPLES 1–4 and 6–8, and Comparative Examples 1–2

As a blood treating filter layer for the purpose of leucocyte removal (hereinafter referred to as leucocyte removal filter layer), a nonwoven fabric (coarseness 66 g/m$^2$, thickness 0.4 mm) made of a polyester (PET: density 1.38 g/cm$^3$) fiber having a mean diameter of 1.7 μm was used in a two-ply, which had a width of 150 mm and a length of b (mm) shown in Table 1. A mesh (mesh size,8 mm, thickness d mm) made of polyethylene with a width of 150 mm was also used as a spacer layer. Both layers were wound around a cylindrical mesh (mesh size 8 mm, thickness 1.0 mm, outer diameter 2r mm) made of polyethylene being overlapped each other, so that, when they were wound like a roll, the spacer layer was overlapped with an outer filter layer by a spacer section length of n (mm) from an outer end of the filter layer and a part of the spacer layer was exposed on the most outer filter layer, to give a hollow cylindrical filter material with an outer diameter of 36 mm as shown in FIG. 5.

Both end faces along the cylindrical axis of this filter material were sealed with a urethane. Then, the filter material was installed in a cylindrical polycarbonate case with an inner diameter of 41 mm and a length of 150 mm, which had a blood inlet and a blood outlet in the top part and the bottom part of the case, respectively, so that an outer and an inner circumferential surfaces of the filter material communicated with the blood inlet and the blood outlet of the case, respectively, to give a leucocyte removal filter equipment.

EXAMPLE 5

As a leucocyte removal filter layer, a porous material (mean pore size 30 μm, thickness 1.0 mm) made of a polyvinylformal with a width of 150 mm and a length of 680 mm was used. Also a mesh made of polyethylene (mesh size 8 mm, thickness 1.0 mm) with a width of 150 mm and a length of spacer section of 550 mm was used as a spacer layer. These two layers were wound as in Example 1–4, to give a hollow filter material with an outer diameter of 36 mm as shown in FIG. 5.

Both end faces along the cylindrical axis of this filter material were sealed with a urethane. Then, the filter material was installed in a cylindrical polycarbonate case with an inner diameter of 41 mm and a length of 150 mm, which had a blood inlet and a blood outlet in the top part and the bottom part of the case, respectively, so that an outer and an inner circumferential surfaces of the filter material communicated with the blood inlet and the blood outlet of the case, respectively, to give a leucocyte removal filter equipment.

COMPARATIVE EXAMPLE 1

As a leucocyte removal filter layer, a nonwoven fabric (coarseness 66 g/m$^2$, thickness 0.4 mm) made of a polyester (PET: density 1.38 g/cm$^3$) fiber having a mean diameter of 1.7 μm was used in a two-ply, which had a width of 150 mm and a length of 680 mm.

This layer was wound around a cylindrical mesh made of polyethylene (mesh size 8 mm, thickness 1.0 mm, outer diameter 22 mm), to give a hollow cylindrical filter material with an outer diameter of 36 mm.

Both end faces along the cylindrical axis of this filter material were sealed with a urethane. Then, the filter material was installed in a cylindrical polycarbonate case with an inner diameter of 41 mm and a length of 150 mm, which had a blood inlet and a blood outlet in the top part and the bottom part of the case, respectively, so that an outer and an inner circumferential surfaces of the filter material communicated with the blood inlet and the blood outlet of the case, respectively, to give a leucocyte removal filter equipment.

COMPARATIVE EXAMPLE 2

As a leucocyte removal filter layer, a nonwoven fabric (coarseness 66 g/m$^2$, thickness 0.4 mm) made of a polyester (PET: density 1.38 g/cm$^3$) fiber having a mean diameter of 1.7 μm was used in a two-ply, which had a width of 150 mm and a length of 680 mm. A mesh (mesh size 8 mm, thickness 2 mm) made of polyethylene was also used as a spacer layer with a width of 150 mm and a length of 380 mm. Both layers were wound around a cylindrical mesh (mesh size 8 mm, thickness 1.0 mm, outer diameter 8.0 mm) being overlapped each other, so that, when they were wound like a roll, the spacer layer was overlapped with an outer filter layer by the spacer section length of 380 mm from an outer end of the filter layer and the spacer layer was not exposed at the outer end, to give a hollow cylindrical filter material with an outer diameter of 36 mm.

Both end faces along the cylindrical axis of this filter material were sealed with a urethane. Then, the filter material was installed in a cylindrical polycarbonate case with an inner diameter of 41 mm and a length of 150 mm, which had a blood inlet and a blood outlet in the top part and the bottom part of the case, respectively, so that an outer and an inner circumferential surfaces of the filter material communicated with the blood inlet and the blood outlet of the case, respectively, to give a leucocyte removal filter equipment.

EXPERIMENTAL EXAMPLE 1

Three liters of fresh bovine blood (leucocyte count 4,800–6,800 cells/$\mu$l, platelet count 163,000–239,000 platelets/$\mu$l) added with heparin (4,000 U/l) as an anticoagulant was passed through each of the filters of the Examples and Comparative Examples described above at 37° C. and at the flow rate of 50 ml/min using a blood pump, then leucocyte removal rates and pressure losses of the equipments before and after the filtration were studied.

Blood samples were collected at each of inlets and outlets of the filter equipments followed by counting their leucocyte counts [cell/$\mu$l] using the Turk's staining method. Leucocyte removal rates were calculated from the values of the leucocyte counts as follows:

Leucocyte removal rate [%]=(Leucocyte count of the blood at the inlet side−Leucocyte count of the blood at the outlet side)×100 /leucocyte count of the blood at the inlet side Pressure losses were obtained by connecting pressure gauges in both the inlet and outlet sides of the blood circuit of the equipment and calculating as follows:

Pressure loss [mmHg]=Pressure at the inlet side−Pressure at the outlet side

Leucocyte removal treatments were tried by passing 3 liters of the blood to be treated each at the flow rate of 50 ml/min. An index for a resistance for filter blocking due to activated blood coagulation components was evaluated as a rate of the number of runs in which the blood treatments were achieved with pressure losses of the equipment under 150 mmHg. Each experiment was carried out with 15 runs.

Specifications of the filters used in the Examples and the Comparative Examples and their results are shown in Table 1 and Table 2 respectively. In these Tables, the term "Length of Spacer Sections" means a length of overlapped part of the mesh between the leucocyte removal filter layers and is expressed by a length of the filter layer in contact with the mesh, excluding an exposed part on the outermost and/or innermost circumferential surface of the filter, material. And the term "Flow Achieving Rates" shows an achieving rate of the blood treatments in which 3 liters of blood could be treated without experiencing a pressure loss of 150 mmHg or higher. Furthermore, the specification of each,filter material was evaluated by calculating a total performance index which was a value obtained by dividing a product of the Leucocyte Removal Rate and the Flow Achieving Rate by 100.

EXAMPLE 9

As a leucocyte removal filter layer, a nonwoven fabric (coarseness 66 g/m$^2$, thickness 0.4 mm) made of a polyester (PET: density 1.38 g/cm$^3$) fiber having a mean diameter of 1.7 $\mu$m was used in a two-ply, which had a width and a length of 40 mm and 60 mm, respectively. A mesh (mesh size 8 mm) made of. polyethylene was also,used as a spacer layer with a width of 40 mm. Both layers were wound like a roll so that, when they were wound like a roll, the spacer layer was overlapped with the outer filter layer by a spacer section length of 60 mm from the outer end of the filter layer and a part of the spacer layer was exposed on the outermost filter layer, to give a hollow cylindrical filter material with an outer diameter of 11 mm and an inner diameter of 6 mm as shown in FIG. 4.

Both end faces along the cylindrical axis of this filter material were sealed with a urethane. Then, the filter material was installed in a cylindrical polypropylene case with an inner diameter of 13 mm and a length of 45 mm, which had a blood inlet and a blood outlet in the top part and the bottom part of the case, respectively, so that an outer and an inner circumferential surfaces of the filter material communicated with the blood inlet and the blood outlet of the case, respectively, to give a leucocyte removal filter equipment.

COMPARATIVE EXAMPLE 3

As a leucocyte removal filter layer, a nonwoven fabric (coarseness 66 g/m$^2$, thickness 0.4 mm) made of a polyester (PET: density 1.38 g/cm$^3$) fiber having a mean diameter of 1.7 $\mu$m was used in a two-ply, which had a width of 40 mm and a length of 60 mm. This layer was wound like a roll to give a hollow cylindrical filter material with an outer diameter of 11 mm and an inner diameter of 8 mm.

Both end faces along the cylindrical axis of this filter material were sealed with a urethane. Then, the filter material was installed in a cylindrical polypropylene case with an inner diameter of 13 mm and a length of 45 mm, which had a blood inlet and a blood outlet in the top part and the bottom part of the case, respectively, so that an outer and an inner circumferential surfaces of the filter material communicated with the blood inlet and the blood outlet of the case, respectively, to give a leucocyte removal filter equipment.

EXPERIMENTAL EXAMPLE 2

Fifteen milliliters of human fresh blood (leucocyte count 4,650 cells/$\mu$l, platelet count 204.000 platelets/$\mu$l) added with ACD-A as an anticoagulant was passed through each of the filter equipments of the Example 9 and the Comparative Example 4 at the flow rate of 1 ml/min using a blood pump, then leucocyte removal rates before,and after the filtration and also concentrations of PF4 ( platelet 4th factor) and $\beta$-TG ($\beta$-thromboglobulin).as indices for activities of the platelet before and after the filtration were measured.

Blood samples were collected at each of the inlets and the outlets of the filter equipments followed by counting their leucocyte counts [cell/$\mu$l] using the Turk's staining method. Leucocyte removal rates were calculated from the values of the leucocyte counts as follows:

Leucocyte removal rate [%]=(Leucocyte count of the blood at the inlet side−Leucocyte count of the blood at the outlet side)×100 /leucocyte count of the blood at the inlet side Results are shown in Table 3.

It is found that the activation of platelet is inhibited in the cases of the filter material structures of the present invention compared with the conventional filter structures.

TABLE 1

|  | 2R Outer Diameter of Filter Section (mm) | 2r Inner Diameter of Filter Section (mm) | L Width of Filter or Spacer Section (mm) | V Volume of Filter Section (mm³) | b Length of Leucocyte Removal Layer (mm) | d Thickness of Spacer Section (mm) | n Length of Spacer Section (mm) | D Volume Ratio of Spacer Section |
|---|---|---|---|---|---|---|---|---|
| Example 1 | 36 | 8 | 150 | 145000 | 680 | 1.0 | 550 | 0.57 |
| Example 2 | 36 | 8 | 150 | 145000 | 680 | 1.0 | 340 | 0.45 |
| Example 3 | 36 | 16 | 150 | 123000 | 680 | 0.5 | 650 | 0.40 |
| Example 4 | 36 | 8 | 150 | 145000 | 380 | 2.0 | 340 | 0.70 |
| Example 5 | 36 | 8 | 150 | 145000 | 680 | 1.0 | 550 | 0.57 |
| Example 6 | 36 | 18 | 150 | 115000 | 680 | 0.3 | 650 | 0.26 |
| Example 7 | 36 | 8 | 150 | 145000 | 680 | 1.0 | 120 | 0.12 |
| Example 8 | 36 | 8 | 150 | 145000 | 320 | 2.5 | 300 | 0.78 |
| Comparative Example 1 | 36 | 22 | 150 | 96000 | 680 | 0.0 | 0 | 0.00 |
| Comparative Example 2 | 36 | 8 | 150 | 145000 | 380 | 2.0 | 340 | 0.70 |

TABLE 2

|  | A Leucocyte Removability (%) | B Flow Achieving Rate (%) | C Total Performance Index (A × B)/100 |
|---|---|---|---|
| Example 1 | 97.6 | 100 | 97.6 |
| Example 2 | 98.5 | 80 | 78.8 |
| Example 3 | 98.1 | 87 | 85.3 |
| Example 4 | 91.5 | 100 | 91.5 |
| Example 5 | 96.5 | 100 | 96.5 |
| Example 6 | 97.0 | 53 | 51.4 |
| Example 7 | 98.5 | 60 | 59.1 |
| Example 8 | 58.6 | 100 | 58.6 |
| Comparative Example 1 | 98.9 | 33 | 32.6 |
| Comparative Example 2 | 92.2 | 40 | 36.9 |

TABLE 3

|  | Leucocyte Removability (%) | PF4 (ng/ml) | β-TG (ng/ml) |
|---|---|---|---|
| Example 9 | 97.6 | 102 | 976 |
| Comparative Example 4 | 100 | 208 | 1620 |

INDUSTRIAL APPLICABILITY

Since the blood treating filter equipment of the present invention does not show a blocking of the filter material due to activated coagulation components in the blood even when a large amount of blood on the order of several liters is treated, removal of target substances from a total amount of a desired volume of blood can be performed at high efficiency.

What is claimed is:

1. A filter for filtering blood, comprising:
   a coiled core with a hollow center, said core having a blood filter layer having a first surface and a second surface opposite said first surface and a spacer layer having a third surface and a fourth surface opposite said third surface, blood flowing more easily through said spacer layer than through said blood filter layer, wherein both ends of said blood filter and surface layers are sealed,
   one of said first surface of said blood filter layer and said fourth surface of said spacer layer defining an outer circumference of said coiled core,
   said blood filter layer and said spacer layer being coiled so that inside said coiled core said first surface of said blood filter directly contacts said third surface of said spacer layer and said second surface of said blood filter layer directly contacts said fourth surface of said spacer layer;
   said blood filter layer comprising a nonwoven fabric made of fibers having a mean diameter of not less than 0.3 µm and less than 5.0 µm; and
   a casing having a blood inlet in fluid communication with said outer circumference of said coiled core and a blood outlet in fluid communication with said hollow center, wherein blood entering said blood inlet proceeds in two paths to said blood outlet, a first path within said spacer layer and a second path transversely across said blood filter layer and said spacer layer.

2. The filter of claim 1, wherein said blood filter layer completely surrounds said hollow center.

3. The filter of claim 2, further comprising a porous layer interior to said blood filter layer that completely surrounds said hollow center.

4. The filter of claim 1, wherein a volume ratio of said spacer layer is not less than 0.3 and not more than 0.7.

5. The filter of claim 1, wherein said spacer layer has a thickness not less than 0.5 mm and not more than 2 mm.

6. The filter of claim 1, wherein said blood filter layer is a leucocyte removal filter layer.

7. The filter of claim 1, wherein a length of said coiled core between end faces thereof is from two to ten times an outer diameter of said coiled core.

8. The filter of claim 1, wherein said blood filter layer comprises plural layers.

9. A filter for filtering blood, comprising:
   a coiled core with a hollow center, said core having only two layers that are coiled atop one another, said two layers being a blood filter layer and a spacer layer, blood flowing more easily through said spacer layer than through said blood filter layer, wherein ends of said blood filter and spacer layers are sealed and said blood filter layer comprises a nonwoven fabric made of fibers having a mean diameter of not less than 0.3 µm and less than 5.0 µm, an outer side of said spacer layer defining an outer circumference of said coiled core, said blood filter layer and said spacer layer being coiled so that both sides of said blood filter layer directly contact respective sides of said spacer layer interior to said coiled core; and a casing having a blood inlet in fluid communication with said outer side of said spacer layer at said outer circumference of said coiled core and a blood outlet in fluid communication with said hollow center, wherein blood entering said blood inlet proceeds to said blood outlet both within said spacer layer and transversely across said blood filter layer and said spacer layer.

10. The filter of claim 9, wherein said blood filter layer completely surrounds said hollow center.

11. The filter of claim 10, further comprising a porous layer interior to said blood filter layer that completely surrounds said hollow center.

12. The filter of claim 9, wherein a volume ratio of said spacer layer is not less than 0.3 and not more than 0.7.

13. The filter of claim 9, wherein said spacer layer has a thickness not less than 0.5 mm and not more than 2 mm.

14. The filter of claim 9, wherein said blood filter layer is a leucocyte removal filter layer.

15. The filter of claim 9, wherein a length of said coiled core between end faces thereof is from two to ten times an outer diameter of said coiled core.

16. The filter of claim 9, wherein said blood filter layer comprises plural layers.

17. The filter of claim 9 further comprising a support layer around said coiled core.

18. The filter of claim 17 wherein said support layer is an extension of said spacer layer.

19. The filter of claim 17 wherein said support layer is independent of said spacer layer.

20. A filter for filtering blood, comprising:

a coiled core with a hollow center, said core having only two layers that are coiled atop one another, said two layers being a blood filter layer and a spacer layer, blood flowing more easily through said spacer layer than through said blood filter layer, wherein ends of said blood filter and spacer layers are sealed and said blood filter layer comprises a nonwoven fabric made of fibers having a mean diameter of not less than 0.3 $\mu$m and less than 5.0 $\mu$m, an outer side of said blood filter layer defining an outer circumference of said coiled core, said blood filter layer and said spacer layer being coiled so that both sides of said blood filter layer directly contact respective sides: of said spacer layer interior to said coiled core; and a casing having a blood inlet in fluid communication with said outer side of said blood filter layer at said outer circumference of said coiled core and a blood outlet in fluid communication with said hollow center, wherein blood entering said blood inlet proceeds to said blood outlet both within said spacer layer and transversely across said blood filter layer and said spacer layer.

21. The filter of claim 20, wherein said blood filter layer completely surrounds said hollow center.

22. The filter of claim 21, further comprising a porous layer interior to said blood filter layer that completely surrounds said hollow center.

23. The filter of claim 20, wherein a volume ratio of said spacer layer is not less than 0.3 and not more than 0.7.

24. The filter of claim 20, wherein said spacer layer has a thickness not less than 0.5 mm and not more than 2 mm.

25. The filter of claim 20, wherein said blood filter layer is a leucocyte removal filter layer.

26. The filter of claim 20, wherein a length of said coiled core between end faces thereof is from two to ten times an outer diameter of said coiled core.

27. The filter of claim 20, wherein said blood filter layer comprises plural layers.

* * * * *